United States Patent [19]
Tripp et al.

[11] Patent Number: 5,273,047
[45] Date of Patent: Dec. 28, 1993

[54] TRANSDUCER HOUSING WITH A CALIBRATION PORT

[75] Inventors: Carl F. Tripp, Costa Mesa, Calif.; Fred P. Lampropoulos, Salt Lake City, Utah; Steven R. Taylor, Salt Lake City, Utah; William Padilla, Salt Lake City, Utah; Marshall T. Denton, Salt Lake City, Utah

[73] Assignee: Merit Medical Systems, Inc., Salt Lake City, Utah

[21] Appl. No.: 28,997

[22] Filed: Mar. 10, 1993

[51] Int. Cl.$^5$ ............................................. A61B 5/0215
[52] U.S. Cl. ..................... 128/675; 128/748; 73/740; 73/4 R
[58] Field of Search .................. 128/673–675, 128/748; 73/4 R, 706–708, 715, 740

[56] References Cited

U.S. PATENT DOCUMENTS

| | | | |
|---|---|---|---|
| 3,628,526 | 12/1971 | Bigliano | 128/748 |
| 4,557,269 | 12/1985 | Reynolds et al. | 128/675 |
| 4,576,181 | 3/1986 | Wallace et al. | 128/748 X |
| 4,610,256 | 9/1986 | Wallace | 128/675 |
| 4,672,974 | 6/1987 | Lee | 128/748 X |
| 4,825,876 | 5/1989 | Beard | 128/675 |
| 4,873,986 | 10/1989 | Wallace | 128/675 X |
| 4,920,972 | 5/1990 | Frank et al. | 128/675 |
| 5,086,777 | 2/1992 | Hishii | 128/675 |

OTHER PUBLICATIONS

NAMIC ®Perceptor ™ DT Brochure, Jul. 1991.

*Primary Examiner*—Angela D. Sykes
*Attorney, Agent, or Firm*—Workman Nydegger Jensen

[57] ABSTRACT

A novel pressure transducer apparatus for medical pressure monitoring apparatus having a housing with a calibration port. The patient side of the transducer senses fluid pressures to be monitored. The non-patient side of the transducer is hermetically sealed in the housing of the apparatus. The housing has a female calibration port communicating, via a pinhole, with the non-patient side of the transducer. The non-patient side of the transducer can thus alternatively be vented to atmospheric pressure or be exposed to a vacuum calibration pressure.

36 Claims, 4 Drawing Sheets

TRANSDUCER HOUSING WITH A CALIBRATION PORT

I. BACKGROUND

A. Field of the Invention

The present invention relates to pressure transducers for medical use. More particularly, the present invention relates to devices and methods used for calibrating a disposable pressure transducer adapted for medical use in direct measurement of blood pressures and the like.

B. The Prior State of the Art

One of the most frequently measured conditions of a patient undergoing an evaluation, diagnosis or treatment is the patient's blood pressure. There are generally two types of methods used for measuring and/or monitoring blood pressure, namely, indirect blood pressure measurement, and direct blood pressure measurement. Indirect blood pressure measurement techniques are based on non-invasive procedures such as using a pressure cuff and a stethoscope. Direct blood pressure measurement techniques, on the other hand, are made by using invasive techniques which permit intracorporeal measuring and monitoring of blood pressures.

Notably, when diagnosing and treating critically ill patients, direct blood pressure measurements are almost always preferred over indirect blood pressure measurements due to several factors. First, use of direct blood pressure measurement greatly increases the accuracy of the blood pressure reading. Second, direct measurement facilitates the continuous monitoring of a patient's blood pressure as opposed to intermittent monitoring. Third, direct blood pressure measurement enables rapid detection of any change of cardiovascular activity, which may be of particular importance in emergency situations. Fourth, direct blood pressure measurement can also readily be used to measure and monitor a patient's blood pressure at specific internal locations, such as within the chambers of the heart. Because of these and other advantages, therefore, direct blood pressure measurement and monitoring has become a routine procedure in treating critically ill patients.

Direct blood pressure measurement and monitoring typically involves catheterization. A hollow needle or cannula is first inserted into a peripheral blood vessel. For example, in the case of monitoring arterial blood pressure, it is inserted into a radial artery. If venous blood pressure is to be monitored, the needle is inserted into the antecubital, radial, tubular or subclavian vein. A catheter is filled with a sterile saline solution and de-bubbled. The catheter is then threaded through the needle and into the particular blood vessel. The catheter may then be guided along the blood vessel until the tip of the catheter is positioned at a particular point within the body at which it is desired to make the blood pressure measurement. With the catheter thus in place, the needle may be withdrawn and the entry site of the catheter is taped down.

Prior to positioning the proximal end of the indwelling catheter within the patient as described above, the distal end of the catheter is connected to pressure tubing that in turn is connected to a pressure transducer. The catheter is generally also connected to a suitable continuous flush device or heparin drip to prevent clotting around the tip of the catheter. The pressure transducer is in turn electrically connected to a monitor and/or other output devices near the patient's bedside which display the patient's blood pressure waveform using analog and/or digital readouts.

When setting up the blood pressure measurement system as described above, it is important to prime the catheter and the tubing with the sterile solution in a way so that any air bubbles within the catheter and tubing are removed, thus providing a continuous fluid column that runs from the tip of the catheter to the pressure transducer. Then, when the catheter is positioned within the patient's blood vessel, as the patient's heart pumps blood, periodic pressure pulses are transmitted through the patient's blood vessel and along the incompressible fluid column in the catheter to the pressure transducer. The transducer generates electrical signals representing the pressure pulses, and those signals are then amplified and displayed on the appropriate monitor and/or output devices. Usually, in such a system a display monitor is used to show the patient's blood pressure as a function of time. This type of display being commonly referred to as the blood pressure waveform. This blood pressure waveform is used by medical personnel to appropriately diagnose and treat the patient.

One of the most important components of the abovedescribed blood pressure monitor system is the pressure transducer. Significantly, the accuracy and the precision of the pressure transducer set an upper limit to the quality of the blood pressure data which can be obtained. Accordingly, pressure transducers for this type of application have been developed which have a high degree of reliability, sensitivity and accuracy. Typically, transducers for this type of application are comprised of piezoresistive semiconductor integrated circuits or "chips." These transducers have a thin diaphragm which, on one side, is in fluid communication with the sterile fluid column contained in the catheter and tubing. This thin diaphragm is deflected by the pressure pulses which travel through the fluid column in the catheter and tubing. As the diaphragm is flexed by virtue of the pressure pulses, the electrical resistance of the diaphragm changes in proportion to the amount by which the diaphragm is flexed, and appropriate electronic circuitry generates an electrical signal representing the pressure exerted on the diaphragm. In this way, the blood pressures are transformed into a suitable electrical signal or waveform.

In order to assure accuracy of pressure measurement, the transducer should be calibrated at a zero pressure by a process called "zeroing." Zeroing a transducer is important in that falsely reported pressures will yield inaccurate data that is unreliable for purposes of evaluating and/or diagnosing a patient's condition. Calibrating a transducer may be done frequently, depending on the reliability of the particular transducer being used. Reliability is affected by the transducer's propensity to produce drift or change in its output signals incident to stress from excess pressure or from thermal changes.

Transducers can be calibrated from either the front or the backside, the front side being the side that is in fluid communication with the sterile fluid column of the catheter and tubing. The backside is the side of the transducer diaphragm that is not in contact with the sterile fluid column. By exerting a known positive pressure on the front side, a display device can be read to determine if the transducer is reading at the known pressure. Conversely, by exerting a known negative pressure or vacuum on the backside of the transducer, an effect equivalent to a known positive pressure on the front side is achieved, and again, the display device can then be read. In either technique, the accuracy and need for calibration is judged by the degree of deviation of the actual transducer pressure reading as compared to the applied and known pressure. Adjustments to the monitor can then be made as necessitated and dictated by the reading, to calibrate the transducer.

There are various difficulties and hazards with calibrating a transducer by using the front or patient side that is in direct contact with the sterile fluid column that is intravenously situated in the patient. Ordinarily, calibration is done by an instrument that introduces pressure to the transducer by a fluid medium such as air. Difficulties and hazards of patient side calibration arise from the potentiality for entry of air and/or contaminants into the patient's intravenous system. The entry of air and contaminants are a potential cause of embolisms and infection. Thus, it is desirable to avoid transducer calibration on the patient side of the transducer.

Also known in the art is backside, or non-patient side, calibration. Backside calibration avoids the undesirable aspects of patient side calibration by means of applying negative pressure to the backside of the transducer, which is isolated from the intravenous fluid column. Backside vacuum pressure is equally effective as patient side positive pressure for calibrating the transducer, while avoiding the complications of non-sterility and air emboli, which are known hazards in front side calibration techniques.

One type of backside calibration apparatus is disclosed in U.S. Pat. No. 4,610,256 to Wallace. A cable electrically connects a pressure transducer to a microprocessor, which in turn numerically quantifies the signals output from the transducer. In addition to electrically conductive wires, the cable has an air space running along its length for communication of vacuum pressure through the cable to the backside of the transducer, for the purpose of effecting calibration of the transducer. While the Wallace disclosure uses backside calibration to avoid the aforementioned hazards inherent to patient side calibration, Wallace is not without drawbacks in its disclosed technique.

The cable used to introduce the negative calibration pressure is one source of such drawbacks in that such a cable is expensive to manufacture. The cost of manufacturing mitigates against the economics required of items intended to be deposed of after use. In addition to the manufacturing expense, the cable is also generally difficult to manufacture. Further, attachment of the cable to the transducer is manually difficult, in that if the cable is secured too tightly the air space provided through the cable may be altogether pinched off, thus precluding the backside pressure required for calibration. Thus, to avoid this result, the cable connection must be loosely connected. Of course, a loosely connected cable in itself has inherent problems. Should the cable be inadvertently bumped, pulled upon or jarred, the electrical connection to the transducer can be disrupted.

II. OBJECTS OF THE INVENTION

The present invention seeks to overcome the above described difficulties and disadvantages which have been experienced in the prior state of the art, and seeks to realize a number of important objects and advantages so as to further advance the state of the art in connection with direct blood pressure monitoring techniques, and specifically in connection with calibration techniques for disposable blood pressure transducers.

Briefly summarized, the principal objects and advantages of the invention are as follows.

One important object of the present invention is to provide a disposable pressure transducer that has a housing which contains the transducer and wherein the housing is designed so as to be easily and quickly connected to a mechanism which can be used to apply a negative calibration pressure to the backside of the transducer diaphragm, thereby eliminating the need for application of calibration pressure through the electrical transducer cable.

Another related object of the present invention is to provide a disposable pressure transducer with a housing which can be connected to a standard calibration apparatus without the need for specialized interconnection parts.

Still a further related object of the present invention is to provide a disposable pressure transducer which provides the aforementioned objects, but while still reducing the complexity of manufacturing the transducer housing as well as reducing the complexity and difficulty of assembling the various parts contained within the transducer housing, including the connection of the electrical transducer cable.

Yet another important object of the present invention is to provide a housing for a disposable pressure transducer that provides a calibration port for connection to standardized calibration equipment used for applying a negative calibration pressure to the backside of the transducer diaphragm, and wherein the transducer housing can be easily and comfortably strapped to a patient's arm or mounted to an organizer on an IV pole without causing any encumbrance due to the calibration port.

Still a further important object of the present invention is to provide a transducer housing that has a calibration port through which negative calibration pressure can be applied to the transducer diaphragm which is so designed and placed on the transducer housing in a way that minimizes the potentiality of any liquids entering the port and rendering the transducer inoperative by subjecting the backside of the transducer diaphragm to any such liquids.

These and other objects and features of the present invention will become more fully apparent from the following description and appended claims taken in conjunction with the accompanying drawings, or from the practice of the invention.

Briefly summarized, the foregoing objects and advantages of the present invention are realized in a disposable pressure transducer apparatus that has a housing that is formed from top and bottom members that are joined together. The top and bottom members of the housing together provide a transducer chamber and also a fluid passageway for containing a pressurized fluid, the pressure of which is to be monitored. A pressure monitoring port provides communication of fluid pressures in the fluid passageway to the transducer chamber. A semi-conductor transducer chip is disposed in the transducer chamber. The semi-conductor chip has a diaphragm formed on the chip for sensing the fluid pressures. The front side of the diaphragm senses fluid pressures through the fluid pressure monitoring port and is hermetically sealed in the transducer chamber.

The housing of the apparatus also provides a female calibration port which is used for purposes of venting the backside of the transducer diaphragm to atmospheric pressures and which is also used to introduce calibration pressures to the backside of the transducer diaphragm. The female calibration port is, in a preferred embodiment, formed in the bottom member of the housing and is provided in the form of a female luer slip fitting. A small pinhole is placed in the bottom of the female calibration port which serves for communicating the atmospheric pressures or calibration pressures to the transducer chamber and the backside of the transducer diaphragm. The female calibration port is also hermetically sealed so that the backside of the transducer diaphragm will communicate only through the pinhole to atmospheric or calibration pressures. The female calibration port and pinhole placed in the bottom of the calibration port are designed so as to minimize seepage of any liquids through the calibration port to the backside of the transducer. This is preferably accomplished by making sure that the pinhole is small enough to prevent liquids from entering through the pinhole under normal atmospheric pressures, and by also forming a tortuous pathway from the pinhole to the backside of the transducer diaphragm.

BRIEF DESCRIPTION OF THE DRAWINGS

In order to more fully understand the manner in which the above-recited and other advantages and objects of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the invention in its presently understood best mode for making and using the same will be described with additional specificity and detail through the use of the accompanying drawings in which.

DETAILED DESCRIPTION OF THE PRESENTLY PREFERRED EMBODIMENT

The present invention can best be understood by reference to the drawings, in which like parts are designated with like numerals throughout.

Figure 1:
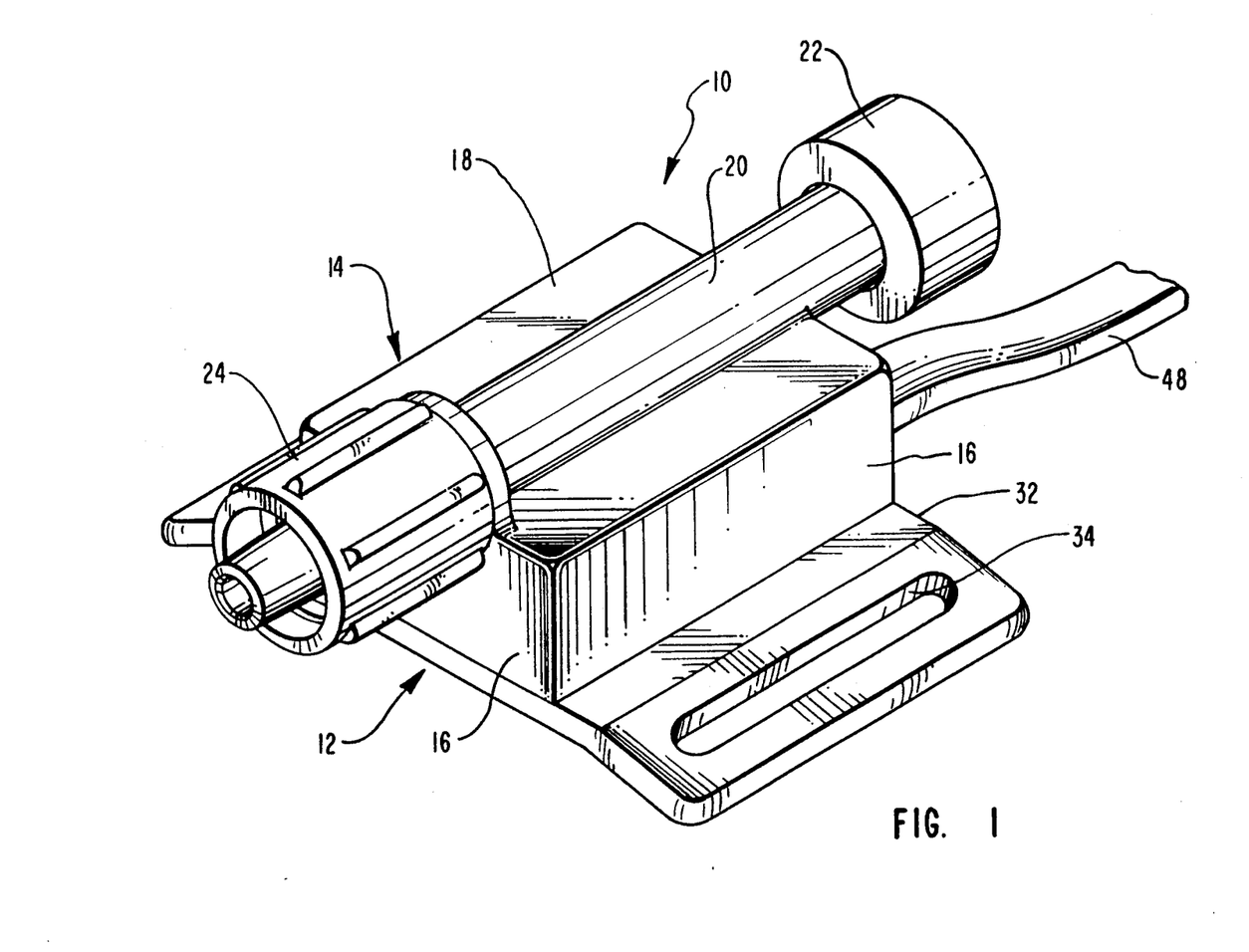
FIG. 1 is a perspective view of the presently preferred embodiment of the blood pressure transducer.
Figure 2:
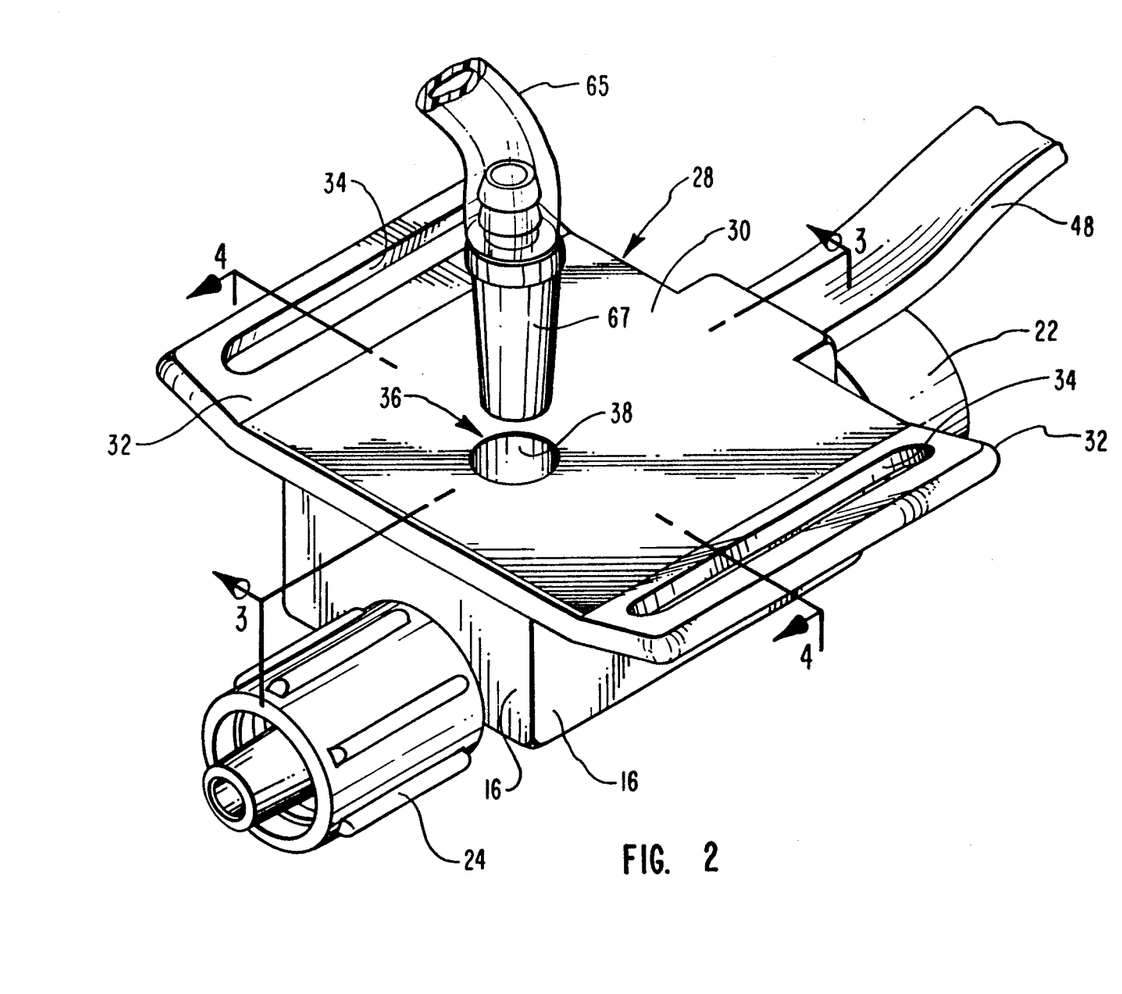
FIG. 2 is a perspective view showing the underside of the presently preferred embodiment of the blood pressure transducer, so as to particularly illustrate the calibration port of the housing.

Reference is first made to FIGS. 1 and 2 which illustrate in perspective view one presently preferred embodiment of the present invention. FIG. 1 shows the assembled apparatus of the present invention from the top side thereof, and FIG. 2 illustrates in perspective view the assembled apparatus with the apparatus turned over so as to more particularly illustrate the bottom of the apparatus and especially the female calibration port.

With reference to FIG. 1, the apparatus is generally designated at 10. In one aspect of the present invention, the apparatus is comprised of a housing means for defining a fluid passageway for containing a pressurized fluid, and for defining a transducer chamber separated from the fluid passageway. In the presently preferred embodiment as illustrated in the drawings, the housing means is generally designated at 12. The housing means 12 could be constructed in a variety of ways, but in the presently preferred embodiment it is comprised of a top member generally designated at 14, and a bottom member which is generally designated at 28 (see FIG. 2. The top and bottom members 14 and 28 of the housing 12 are preferably constructed from unitary pieces that are injection molded from medical grade plastic material. The top member 14 is comprised of a generally rectangular shaped member that has sidewalls 16 and a flat top piece 18, and an open bottom (shown in FIGS. 3 and 4).

Also molded as a unitary part of the top member 14 is a tubular member 20 which runs along the center of the top piece 18. As hereinafter described in greater detail, the tubular member 20 defines a fluid passageway for containing a pressurized fluid column, the pressure of which is to be monitored by the transducer apparatus. Disposed at opposite ends of the tubular member 20 are conventional fittings, as for example, a rotatable threaded male luer fitting 24 on one end, and a threaded female luer fitting 22 on the opposite end. The fittings 22 and 24 provide for coupling of the transducer apparatus to pressure tubing of a type which is commonly known and used in the art in connection with hemodynamic blood pressure monitoring systems or other similar types of pressure monitoring systems. In the case of hemodynamic blood pressure monitoring systems, the luer fitting 24 will typically be connected through tubing to a catheter which is inserted into the patient for purposes of either arterial or venous blood pressure monitoring.

As will be appreciated by those of skill in the art, while the present invention as illustrated and described is particularly useful for direct blood pressure monitoring, the apparatus of the present invention is not intended to be limited to that use and may be used in connection with other types of medical pressure monitoring applications.

The top member 14 of the housing is also preferably molded of transparent plastic so that the column of liquid contained in the tubular member 20 can be easily visualized for purposes of priming and de-bubbling the system when it is first set up.

As shown best in FIG. 2, the bottom member generally designated at 28 is comprised of a generally flat bottom piece 30 that has optional side members 32 situated at an angle on opposite sides of the bottom piece 30. The side members 32 have slots 34 in them which permit the apparatus to be strapped onto the arm, leg or other parts of a patient. The apparatus can also, however, be mounted onto what is known in the art as a transducer organizer (not shown) which is mounted on an IV stand (not shown) for applications where several transducers are required to be used in the course of the procedure.

Figure 3:
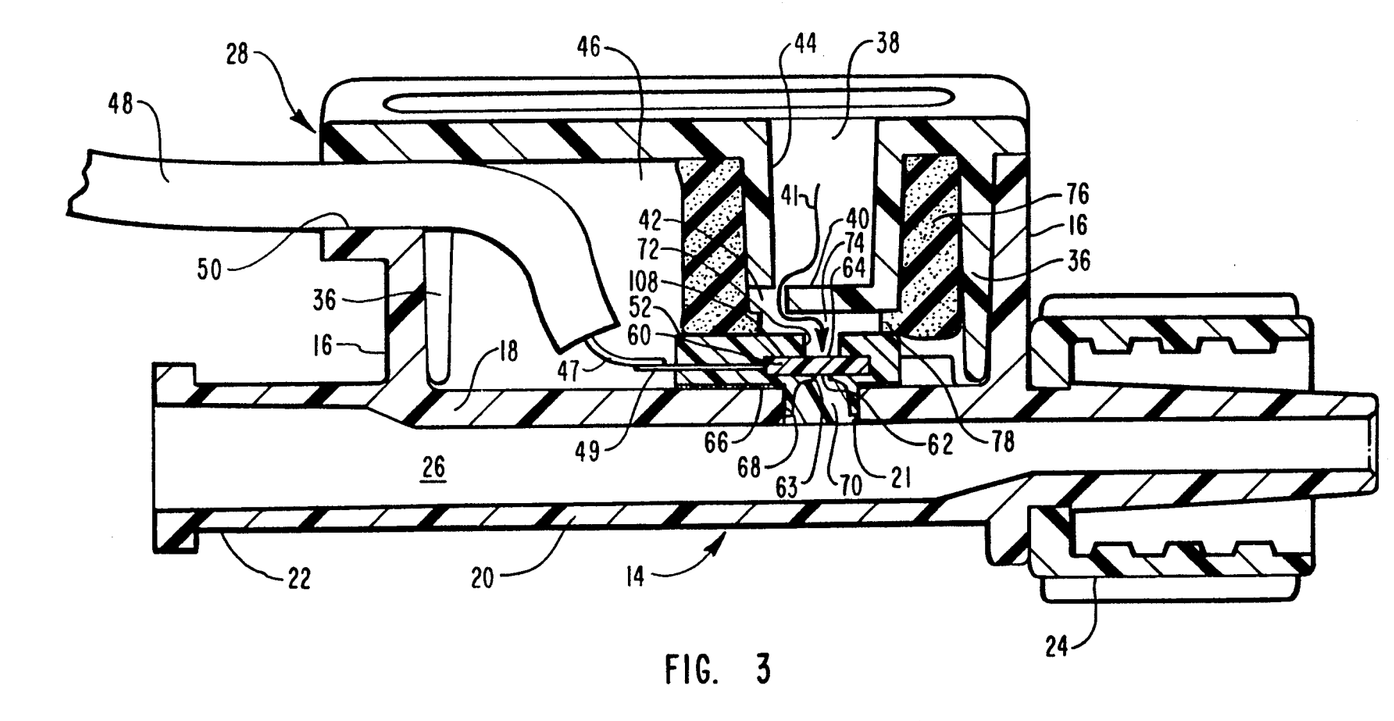
FIG. 3 is a cross-sectional view, taken along the 3—3 line of FIG. 2.
Figure 4:
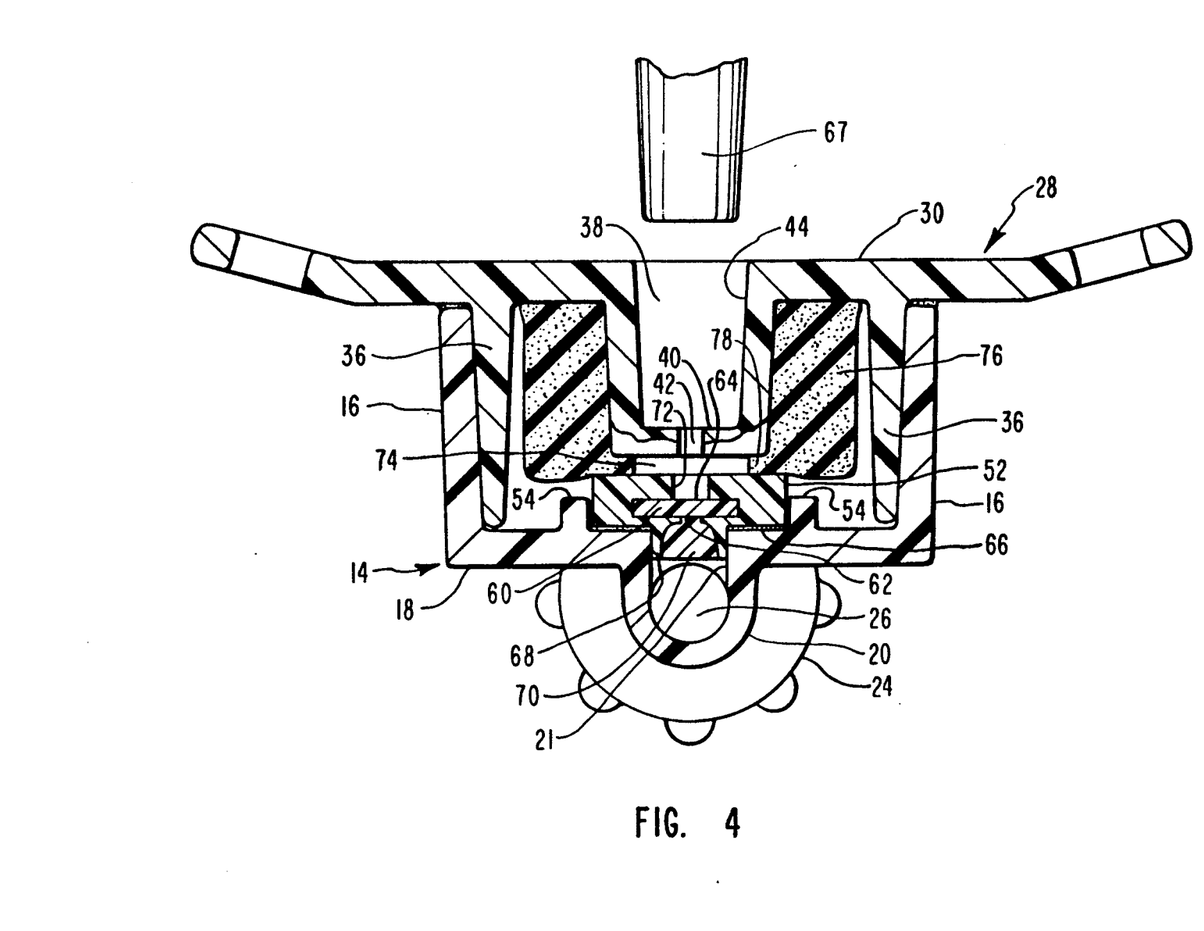
FIG. 4 is an end cross-sectional view, taken along the 4—4 line of FIG. 2.

FIG. 3 is a longitudinal section taken along line 3—3 and FIG. 4 is a lateral sectional view taken along line 4—4 of FIG. 2. As will be appreciated from FIGS. 3 and 4, the sectional views in those drawing figures show the apparatus with the top member 14 oriented toward the bottom of the drawings and the bottom member 28 oriented toward the top of the drawings. Thus, with reference to FIGS. 2-4 taken together, in the presently preferred embodiment the bottom member 28 is also preferably constructed of a unitary piece that is formed by injection molding using a medical grade plastic material or the like. The bottom member 28 has four side walls 37 (two of which are shown in FIGS. 3-4) which are designed to fit immediately inside the sidewalls 16 on the top member 14. Thus, when put together, the top member 14 and bottom member 28 together form an enclosed transducer chamber 46 which is enclosed and separated from the fluid passageway 26, except for a pressure monitoring port means as described below. As further illustrated in FIG. 3, the fluid passageway 26 is separated from the transducer chamber 46 by the top piece which also forms a common wall (see 18 in FIG. 3) with tubular member 20.

In another aspect of the present invention, the apparatus also comprises a pressure monitoring port means for providing communication of fluid pressures in the fluid passageway 26 to the transducer chamber 46. In the preferred embodiment, a pressure monitoring port is formed, for example, by a small circular opening 21 (see FIG. 3) through the common wall 18 which separates the transducer chamber 46 from the fluid passageway 26. The opening 21 which serves as a pressure monitoring port thus provides for communication of fluid pressure from the fluid passageway 26 to the transducer chamber 46, and in particular, to the front side of the transducer diaphragm as more particularly described hereinafter.

In still another aspect of the invention, a transducer means is disposed in transducer chamber 46 for providing electrical signals proportional to fluid pressures sensed in the fluid passageway 26 through the pressure monitoring port provided by opening 21. In the preferred embodiment the transducer means is comprised of a piezoresistive semiconductor integrated circuit or chip as schematically illustrated at 60 in FIG. 3 and 4. The integrated circuit or chip 60 includes electronic components which form the transducer. The integrated circuit 60 also includes a diaphragm that is flexed by the pressure pulses and which, as schematically shown, has a front side 62 and a backside 64.

The integrated transducer circuit 60 is in turn mounted on a chip carrier member 52. The electrical leads 49 extend from the integrated circuit 60 through the chip carrier member 52 so that the leads 49 can be electrically connected to the wires 47 provided in electrical cable 48. The cable 48 is securely bonded and hermetically sealed through an opening or port 50 provided in the top and bottom members 14 and 28.

With continued reference to the sectional views in FIGS. 3 and 4, the chip carrier member 52 includes a bowl-shaped member 68 that fits within the opening 21 of the pressure monitoring port. The bowl-shaped member 68 is filled with a well-known silicon gel material 70 which is commonly used in the art to provide electrical isolation so that the front side 62 of the transducer diaphragm does not come into contact with the liquid contained in the fluid passageway 26. The silicon gel material 70 that is disposed within the bowl-shaped member 68 in effect serves as an isolation means for electrically isolating chip 60 while also providing a fluid coupling with respect to the pressure pulses that are sensed through the fluid column in the fluid passageway 26.

In a further aspect of the invention, the apparatus is comprised of a first hermetic sealing means for creating an airtight seal so that the front side 62 of the transducer diaphragm is in fluid communication only with fluid pressures sensed through the pressure monitoring port 21. In the preferred embodiment, the chip carrier member 52 is hermetically sealed to the common wall 18 by means of a suitable adhesive 66 or by other equivalent means such as ultrasonic bonding or the like. In this way, the front side 62 of the transducer diaphragm is hermetically sealed in the transducer chamber 46 so that the front side 62 of the transducer can only communicate with the sensed fluid pressures in the fluid passageway 26 through the pressure monitoring port 21. The bowl-shaped member 68 has a small aperture 62 which is positioned directly over the front side of the transducer diaphragm 62 so that the front side 62 of the transducer diaphragm is in fluid communication with the sensed fluid pressures by means of the silicon gel material 70, which, in turn, is in direct contact with the fluid column in fluid passageway 26.

Importantly, the apparatus is also comprised of a female calibration port means for providing a vent to atmosphere and for providing communication of calibration pressure to the transducer chamber 46. The female calibration port generally designated 36 (See FIG. 2) is shown in more particular detail in the cross-sectional views of FIGS. 3 and 4. In particular, the female calibration port 36 is formed as a well in the bottom member 28. The well has tapered cylindrical sides 44 and a bottom 40 and an open top 38. Located in the bottom 40 of the well at the juncture of the cylindrical sides 44 with the bottom 40 is a small pinhole 42.

The bottom 40 of the well is spaced slightly above the backside of the chip carrier member 52 so that a small space 74 is located between the two. As will be further seen with reference to FIGS. 3 and 4, the chip carrier member 52 also has a small opening 72 formed in the backside of the chip carrier member 52 which communicates with the backside 64 of the transducer diaphragm. Accordingly, the backside 64 of the transducer diaphragm is, in this manner, vented to atmosphere by means of the opening 72 in the chip carrier member 52, the space 74 and pinhole 42.

Not only is the backside 64 of the transducer diaphragm vented to atmosphere in this way, but calibration pressures are also communicated to the backside 64 of the transducer diaphragm. By attaching a piece of tubing 65 (see FIGS. 2 and 4) with a tapered male fitting 67, tapered male fitting 67 will form a fluid-tight fit in the well above the bottom 40. The tubing 65 in turn may be connected to devices which are well known in the art for providing negative calibration pressures which can be used for zeroing the transducer.

As will be appreciated in reference to FIG. 3, the small pinhole 42 which communicates with the space 74 and opening 72 in the chip carrier member 52 together provide a tortuous pathway (schematically shown at arrow 41) through which the backside 64 of the transducer diaphragm is either vented to atmosphere or through which calibration pressures are introduced. The size of the pinhole 42 is preferably made small enough so that surface tension of liquids, such as sterile saline solutions and the like commonly used in pressure monitoring applications, will not enter through the pinhole 42 at typical atmospheric pressures. The tortuous pathway 41 also provides additional protection with respect to the potentiality for any such liquids ultimately contacting the backside 64 of the pressure transducer. This tortuous pathway 41 is in part provided by the fact that the pinhole 42 is located at a side of the well, whereas the opening 72 in chip carrier member 52 is typically aligned with the center of the bottom 40 of the well 38, as shown best in FIG. 3.

Second hermetic sealing means is provided for creating an airtight seal so that the backside 64 of the transducer diaphragm is in fluid communication only with the calibration port 36. Thus, the backside 64 of the transducer can only communicate with the atmospheric or calibration pressures that are introduced through the pinhole 42 into the space 74 and opening 72. This hermetic seal may be provided in a variety of ways, one presently preferred way being illustrated in FIGS. 3 and 4 by elastomeric cylinder 76 which surrounds the female luer port 36 at the inside of the transducer chamber 46. The elastomeric member 76 is constructed, for example, of silastic, and is dimensioned so that it will tightly fit around the side walls 44, thereby providing a hermetic seal.

As also shown, the elastomeric member 76 is also sealingly compressed between the bottom 40 of the female calibration port and the top of chip carrier member 52 so that a small shoulder 78 of the cylinder 76 hermetically seals the space 74. In this fashion, the backside 64 of the transducer is completely hermetically sealed. However, alternative ways of hermetically sealing the backside 64 of the transducer can also be accomplished, for example, by hermetically sealing with an adhesive or other suitable bonding methods the sidewalls 37 of the bottom member 28 to the sidewalls 16 of the top member 14.

The overall apparatus is assembled by placing the elastomeric member 76 around the sidewalls 44 of the female calibration port 36. The bottom member 28 is then ready for assembly to the top member 14. The chip carrier member 52 with the semi-conductor transducer circuit 60 mounted thereon and with the electrical cable 48 with wiring 47 connected to leads 49, is then placed in the top member 14 between alignment ridges 54 as shown in FIG. 4. The chip carrier member 52 is then adhesively secured or otherwise bonded to provide the hermetic seal 66 as described above, and the top member 14 is then ready for final assembly to bottom member 28. The top member 14 and bottom member 28, as thus assembled, are then placed together in the manner heretofore described and secured by ultrasonic or other suitable forms of bonding to form the completed apparatus.

In its use, the apparatus is connected at one of the fittings such as fitting 24 to pressure tubing that in turn is connected to an indwelling catheter (not shown) or the like, which is filled with a fluid column. Fourth, direct blood pressure many cases constitute a liquid such as sterile saline solution, contrast media, or other similar kinds of liquids which are used to transmit through the liquid column fluid pressures that are to be monitored in the fluid passageway 26. The fluid column is primed and de-bubbled and then the transducer apparatus is zeroed.

Zeroing is done by connecting a piece of pressure tubing 65 with a suitable male fitting 67 which is tapered to provide a fluid or air-tight seal when inserted into the female calibration port 36. A negative calibration pressure is then applied using calibration devices of a type that are well-known in the art to the backside 64 of the transducer by introducing calibration pressure through the small pinhole 42 located in the bottom of the female calibration port. The calibration pressure is communicated through the space 74 that is hermetically sealed by elastomeric member 76 and through the opening 72 in chip carrier member 52 to the backside 64 of the transducer. Once the calibration pressure has been checked on a monitor and appropriate adjustments, if any, have been made to the transducer reading, the pressure tubing 65 and male fitting 67 are then removed so that the backside 64 of the transducer is thereafter continuously vented to atmospheric pressure by means of the opening 72, space 74 and pinhole 42 in the calibration port 36.

Importantly, since the calibration port 36 is provided in the form of a female port, the surface of the bottom piece 30 is smooth and can be strapped directly onto a patient's arm or leg without causing any discomfort. Furthermore, the female calibration port 36 also tends to minimize the likelihood of liquids entering the transducer chamber 46 so as to prevent the backside 64 of the transducer from being contacted and damaged by any such liquids. This protection is further enhanced by the small size of the pinhole 42 which tends to prevent liquids from entering and also by the tortuous pathway 41 which must be traveled by any such liquids in order to reach the backside 64 of the transducer. Placement of the female port 36 on the bottom member 28 of the apparatus also tends to aid in providing such protection.

While the present invention has been described in reference to the presently preferred embodiment and the presently understood best mode as illustrated herein, the invention may be embodied in other specific forms without departing from its spirit or essential characteristics. The described embodiments are thus to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A disposable pressure transducer apparatus for use in measuring hemodynamic pressure and the like, comprising:

housing means for defining a fluid passageway for containing a pressurized fluid, and for defining a transducer chamber separated from the fluid passageway, said housing means comprising a pressure monitoring port means for providing communication of fluid pressures in the fluid passageway to the transducer chamber;

transducer means, disposed in the transducer chamber, for producing electrical signals proportional to fluid pressures sensed in the fluid passageway through the pressure monitoring port means, said transducer means comprising a diaphragm that if flexed in response to the sensed fluid pressures, a front side of the diaphragm disposed over the pressure monitoring port means;

first hermetic sealing means for creating an airtight seal so that the front side of the diaphragm is in fluid communication only with the pressure monitoring port means and the sensed fluid pressure in the fluid passageway;

said housing means further comprising a female calibration port means for providing a vent to atmosphere and for providing communication of calibration pressure to the transducer chamber, said housing means further comprising another port means for providing electrical connection of a cable therethrough to said transducer means;

said transducer means further comprising a backside of the diaphragm in fluid communication with the atmospheric or calibration pressures communicated through the calibration port means; and second hermetic sealing means for creating an airtight seal so that the backside of the diaphragm is in fluid communication only with the calibration port means and the atmospheric or calibration pressures communicated therethrough.

2. An apparatus as defined in claim 1 wherein said housing means comprises top and bottom members which, when joined together, form therebetween the transducer chamber.

3. An apparatus as defined in claim 2 wherein the top member is a single molded piece of plastic material, and wherein the top member comprises a tubular member joined to a generally rectangular shaped member having four sidewalls and a top piece, and an open bottom.

4. An apparatus as defined in claim 3 wherein at least the tubular member is constructed of a transparent plastic material.

5. An apparatus as defined in claim 3 wherein the tubular member and the top of said rectangular shaped member are joined at a common wall, and wherein the pressure monitoring port means comprises an aperture formed in the common wall.

6. An apparatus as defined in claim 3 wherein the bottom member is a single molded piece of plastic material and is comprised of a bottom piece sized to enclose the open bottom of the rectangular shaped member so as to form therein the transducer chamber.

7. An apparatus as defined in claim 3 wherein the bottom member comprises four sidewalls having a generally rectangular shape, and the four sidewalls of the bottom member being adapted to fit within and in sealing engagement with the four sidewalls of the top member.

8. An apparatus as defined in claim 7 wherein the second hermetic sealing means comprises a fluid-tight bond between the sidewalls and the top piece of the top member, with the sidewalls of the bottom member.

9. An apparatus as defined in claim 7 wherein the female calibration port means is formed in the bottom member.

10. An apparatus as defined in claim 9 wherein the female calibration port means comprises a female luer slip fitting in the form of a generally cylindrical, tapered well with a bottom and cylindrical sides, and an open top.

11. An apparatus as defined in claim 10 wherein the bottom of the well has a small pin hole formed at a juncture between the bottom of the well and the cylindrical sides, said pin hole providing communication of atmospheric or calibration pressures to said transducer chamber.

12. An apparatus as defined in claim 11 wherein the pin hole is small enough to prevent passage of liquids at typical atmospheric pressures.

13. An apparatus as defined in claim 11 wherein the second hermetic sealing means comprises an elastomeric member encircling in a fluid tight manner the cylindrical sides of the well inside of the transducer chamber.

14. An apparatus as defined in claim 13 wherein the transducer means comprises a piezoresistive semiconductor chip mounted on a two-sided chip carrier member.

15. An apparatus as defined in claim 14 wherein the chip carrier member is hermetically bonded on one side to a common wall so as to form said first hermetic sealing means, and wherein the other side of said chip carrier member is spaced from the bottom of said well.

16. An apparatus as defined in claim 15 wherein the other side of said chip carrier member has an aperture that communicates with the backside of the transducer diaphragm, and wherein the space between the bottom of the well and said other side of the chip carrier member is hermetically sealed around said aperture by the elastomeric member, so as to provide said second hermetic sealing means.

17. An apparatus as defined in claim 16 wherein the aperture in the other side of the chip carrier member is generally aligned with the center of the bottom of the well, and is not in alignment with the pin hole, so as to form a tortuous path for fluid communication between the outside of the housing means and the backside of the transducer diaphragm.

18. An apparatus as defined in claims 14 or 17 wherein the chip carrier member comprises a bowl adapted to fit within the pressure monitoring port means, said bowl having an opening in the bottom thereof adjacent the front side of the diaphragm, and said bowl containing isolation means for electrically isolating the semiconductor chip from fluids contained in the fluid passageway, while still communicating fluid pressures through the isolating means to the front side of the diaphragm.

19. An apparatus as defined in claim 18 wherein the isolating material comprises a silicone gel type material which fills said bowl.

20. An apparatus comprising:
housing means for defining a fluid passageway for containing a pressurized fluid, and for defining a transducer chamber separated from the fluid passageway, said housing means comprising top and bottom members which, when joined together, form therebetween the transducer chamber, said housing means further comprising a pressure monitoring port means for providing communication of fluid pressures in the fluid passageway to the transducer chamber, and further comprising a female calibration port means for providing a vent to atmosphere and for providing communication of calibration pressure to the transducer chamber, said housing means further comprising another port means for providing electrical connection of a cable therethrough to said transducer means;

a semiconductor transducer means for sensing fluid pressures, and comprising a diaphragm with a front side for sensing fluid pressures communicated through the pressure monitoring port means, and a backside for sensing atmospheric and calibration pressures communicated through the calibration port means, said transducer means being disposed in the transducer chamber;

two-sided carrier means for securing the semiconductor transducer means in the transducer chamber, and comprising isolation means disposed in the pressure monitoring port means for electrically isolating the front side of the diaphragm from fluids contained in the fluid passageway, while still communicating fluid pressures through the isolating means to the front side of the diaphragm;

first hermetic sealing means for creating an airtight seal so that the front side of the diaphragm is in fluid communication only with the pressure monitoring port means and the sensed fluid pressures in the fluid passageway; and second hermetic sealing means for creating an airtight seal so that the backside of the diaphragm is in fluid communication only with the calibration port means and the atmospheric or calibration pressures communicated therethrough.

21. An apparatus as defined in claim 20 wherein the female calibration port means is formed in the bottom member.

22. An apparatus as defined in claim 21 wherein the female calibration port means comprises a female luer slip fitting in the form of a generally cylindrical, tapered well with a bottom and cylindrical sides, and an open top.

23. An apparatus as defined in claim 22 wherein the bottom of the well has a small pin hole formed at a juncture between the bottom of the well and the cylindrical sides, said pin hole providing communication of atmospheric or calibration pressures to said transducer chamber.

24. An apparatus as defined in claim 23 wherein the pin hole is small enough to prevent passage of liquids at typical atmospheric pressures.

25. An apparatus as defined in claims 23 or 24 wherein the second hermetic sealing means comprises an elastomeric member encircling in a fluid tight manner the cylindrical sides of the well inside of the transducer chamber.

26. An apparatus as defined in claim 25 wherein the top member is a single molded piece of plastic material, and wherein the top member comprises a tubular member joined to a generally rectangular shaped member having four sidewalls and a top piece, and an open bottom.

27. An apparatus as defined in claim 26 wherein the tubular member and the top of said rectangular shaped member are joined at a common wall, and wherein the pressure monitoring port means comprises an aperture formed in the common wall.

28. An apparatus as defined in claim 27 wherein the carrier means is hermetically bonded on one side to the common wall so as to form said first hermetic sealing means, and wherein the other side of said carrier means is spaced from the bottom of said well.

29. An apparatus as defined in claim 28 wherein the other side of said carrier means has an aperture that communicates with the backside of the transducer diaphragm, and wherein the space between the bottom of the well and said other side of the carrier means is hermetically sealed around said aperture by the elastomeric member, so as to provide said second hermetic sealing means.

30. An apparatus as defined in claim 29 wherein the aperture in the other side of the carrier means is generally aligned with the center of the bottom of the well, and is not in alignment with the pin hole, so as to form a tortuous path for fluid communication between the outside of the housing means and the backside of the transducer diaphragm.

31. An apparatus as defined in claim 30 wherein the carrier means comprises a bowl adapted to fit within the pressure monitoring port means, said bowl having an opening in the bottom thereof adjacent the front side of the diaphragm, and said bowl containing the isolation means.

32. An apparatus as defined in claim 31 wherein the isolation means comprises a silicone gel type material which fills said bowl.

33. An apparatus as defined in claim 32 wherein at least the tubular member is constructed of a transparent plastic material.

34. An apparatus as defined in claim 33 wherein the bottom member is a single molded piece of plastic material and is comprised of a bottom piece sized to enclose the open bottom of the rectangular shaped member so as to form therein the transducer chamber.

35. An apparatus as defined in claim 34 wherein the bottom member comprises four sidewalls having a generally rectangular shape, and the four sidewalls of the bottom member being adapted to fit within and in sealing engagement with the four sidewalls of the top member.

36. A disposable pressure transducer apparatus for use in measuring hemodynamic pressures and the like, comprising:

housing means for defining a fluid passageway for containing a pressurized fluid, and for defining a transducer chamber separated from the fluid passageway, said housing means comprising top and bottom members which, when joined together, form therebetween the transducer chamber, and further comprising a pressure monitoring port for providing communication of fluid pressures in the fluid passageway to the transducer chamber, and a female calibration port for providing a vent to atmosphere and for providing communication of calibration pressures to the transducer chamber, and wherein the female calibration port is formed in the bottom member in the form of a generally cylindrical, tapered well with a bottom and cylindrical sides, and an open top, the bottom of the well having a small pinhole formed at a juncture between the bottom of the well and the cylindrical sides so as to provide communication of said atmospheric and calibration pressures therethrough to said transducer chamber;

a semi-conductor transducer means for sensing fluid pressures, and comprising a diaphragm with a front side for sensing fluid pressures communicated through the pressure monitoring port, and a backside for sensing atmospheric and calibration pressures communicated through the pinhole of the female calibration port, said transducer means being disposed in the transducer chamber;

carrier means for securing the semi-conductor transducer means in the transducer chamber, and comprising isolation means disposed in the pressure monitoring port for electrically isolating the front side of the diaphragm from fluids contained in the fluid passageway, while still communicating fluid pressure through the isolation means to the front side of the diaphragm, said carrier means further comprising an aperture that communicates with the backside of the transducer diaphragm and wherein said aperture is generally aligned with the center of the bottom of the well and is not in alignment with the pinhole so as to form a tortuous path for fluid communication between the outside of the housing means and the backside of the transducer diaphragm;

first hermetic sealing means for creating an airtight seal so that the front side of the diaphragm is in fluid communication only with the pressure monitoring port and the sensed fluid pressures in the fluid passageway; and second hermetic sealing means for creating an airtight seal so that the backside of the diaphragm is in fluid communication only with the atmospheric or calibration pressures communicated through the pin hole and the aperture of said carrier means.

* * * * *

UNITED STATES PATENT AND TRADEMARK OFFICE
CERTIFICATE OF CORRECTION

PATENT NO. : 5,273,047
DATED : December 28, 1993
INVENTOR(S) : CARL F. TRIPP et al.

It is certified that error appears in the above-indentified patent and that said Letters Patent is hereby corrected as shown below:

Column 2, line 19, "being" should be --is--
Column 2, line 24, "abovedescribed" should be --above-described--
Column 3, line 47, "deposed" should be --disposed--
Column 6, line 3, after "FIG. 2" insert --)--
Column 9, lines 44-45, delete "Fourth, direct blood pressure" and insert --The fluid column will in--

Signed and Sealed this

Twenty-sixth Day of July, 1994

Attest:

BRUCE LEHMAN

Attesting Officer  Commissioner of Patents and Trademarks